United States Patent
Hintzer et al.

(10) Patent No.: US 9,139,496 B2
(45) Date of Patent: Sep. 22, 2015

(54) PROCESS FOR MANUFACTURING PERFLUOROOLEFINS BY PYROLYSIS OF PERFLUOROCARBONS IN THE PRESENCE OF HYDROGEN

(75) Inventors: Klaus Hintzer, Kastl (DE); André Streiter, Muehldorf am Inn (DE); Günther J. Kämpf, Altoetting (DE); Kai Helmut Lochhaas, Neuötting (DE); Michael Jürgens, Moenchengladbach (DE); Oleg Shyshkov, Burgkirchen a. d. Alz (DE); Tilman C. Zipplies, Burghausen (DE); Jürgen Troe, Göttingen (DE); Klaus Luther, Göttingen (DE)

(73) Assignee: 3M INNOVATION PROPERTIES COMPANY, Saint Paul, MN (US)

(*) Notice: Subject to any disclaimer, the term of this patent is extended or adjusted under 35 U.S.C. 154(b) by 151 days.

(21) Appl. No.: 13/805,561

(22) PCT Filed: Jun. 27, 2011

(86) PCT No.: PCT/US2011/041971
§ 371 (c)(1),
(2), (4) Date: Mar. 13, 2013

(87) PCT Pub. No.: WO2012/012113
PCT Pub. Date: Jan. 26, 2012

(65) Prior Publication Data
US 2013/0197281 A1 Aug. 1, 2013

(30) Foreign Application Priority Data
Jun. 30, 2010 (GB) .................................. 1010958.5

(51) Int. Cl.
| | |
|---|---|
| *C07C 17/23* | (2006.01) |
| *C07C 21/18* | (2006.01) |
| *C07C 21/185* | (2006.01) |
| *C07C 17/25* | (2006.01) |
| *C07C 17/278* | (2006.01) |
| *C07C 17/281* | (2006.01) |
| *C07C 17/361* | (2006.01) |

(52) U.S. Cl.
CPC ................ *C07C 17/25* (2013.01); *C07C 17/23* (2013.01); *C07C 17/278* (2013.01); *C07C 17/281* (2013.01); *C07C 17/361* (2013.01)

(58) Field of Classification Search
None
See application file for complete search history.

(56) References Cited

U.S. PATENT DOCUMENTS

| 3,816,552 A | 6/1974 | Hartwimmer |
| 6,919,015 B2 * | 7/2005 | Bauer et al. .................. 205/460 |
| 8,344,190 B2 | 1/2013 | Hintzer et al. |

FOREIGN PATENT DOCUMENTS

| EP | 0 287 219 A1 | 4/1987 |
| EP | 0 371 747 B1 | 1/1994 |
| EP | 0 648 530 A1 | 4/1995 |
| WO | WO 01/58584 A2 | 8/2001 |
| WO | WO 02/06193 A2 | 1/2002 |
| WO | WO 2004/061160 A1 | 7/2004 |

* cited by examiner

*Primary Examiner* — Fereydoun G Sajjadi
*Assistant Examiner* — Medhanit Bahta
(74) *Attorney, Agent, or Firm* — C. Michael Geise (57) ABSTRACT

A process is described of pyrolyzing at least one perfluorinated hydrocarbon, or a material containing at least one perfluorinated hydrocarbon, in the presence of hydrogen, to yield a reaction mixture containing difluorocarbene.

15 Claims, 2 Drawing Sheets

PROCESS FOR MANUFACTURING PERFLUOROOLEFINS BY PYROLYSIS OF PERFLUOROCARBONS IN THE PRESENCE OF HYDROGEN

FIELD

This disclosure relates to a chlorine-free process for manufacturing perfluoroolefins, in particular tetrafluoroethene by thermal decomposition (pyrolysis) of perfluorocarbons in the presence of hydrogen. This disclosure also relates to a process of generating difluorocarbene as a precursor of perfluoroolefins, in particular tetrafluoroethene, by the thermal decomposition (pyrolysis) of perfluorocarbons in the presence of hydrogen.

BACKGROUND

Tetrafluoroethene (TFE) and hexafluoropropene (HFP) are widely used as monomers in the manufacture of plastic and elastomeric fluoropolymers. See, for example, J. Scheirs in Modern Fluoropolymers, Wiley, 1996. The worldwide consumption of TFE exceeds $10^5$ tons/year. HFP is used as a comonomer to manufacture thermoplastic and elastomeric fluoropolymers and as starting material for making hexafluoropropene oxide (HFPO). The worldwide consumption of HFP is estimated to amount to 30,000 tons/year.

There are several known methods for manufacturing TFE and HFP. The most common method involves the thermal pyrolysis of $CHClF_2$ (R-22) at temperatures between 600° C. to 1,000° C. Such a process is described, for example, in U.S. Pat. No. 2,551,573. Since this process employs chlorinated raw materials it leads to partially fluorinated and chlorinated low molecular weight products which are difficult to remove from TFE and HFP. Thus providing high purity TFE involves expensive purification steps. Additionally, hydrochloric acid containing HF as impurity is formed as a by-product in large quantities. The hydrochloric acid either has to be discarded or purified at high costs for use in chemical applications.

Therefore, alternative processes have been developed, which do not employ chlorine-containing raw materials. These processes involve the thermal decomposition of fluorinated materials at high temperatures. For example, U.S. Pat. No. 5,611,896 describes a process where elemental fluorine is reacted with carbon to produce $CF_4$, which is subsequently converted to TFE in a plasma torch in the presence of carbon. WO 2004/061160 A1 discloses a process for preparing TFE that comprises subjecting perfluorocarbon stream to a pyrolysis followed by quenching. The pyrolysis reaction is preferably carried out by adding carbon to the pyrolysis reaction.

SUMMARY

In one aspect, the present description relates to a process comprising pyrolyzing at least one perfluorinated hydrocarbon, or a material containing at least one perfluorinated hydrocarbon, in a pyrolysis zone at a temperature between about 580 K and about 2000 K in the presence of hydrogen to yield a reaction mixture containing difluorocarbene, wherein the hydrogen is present in the pyrolysis zone in a molar ratio from about 0.1 to 8 mol hydrogen per mol of perfluorinated hydrocarbon.

The process may further comprise quenching the reaction mixture comprising difluorocarbene to yield a product mixture containing tetrafluoroethene and/or hexafluoropropene and feeding back into the pyrolysis zone at least a part of the product mixture after removing tetrafluorethene and/or hexafluoropropene therefrom.

In yet another aspect, the material containing at least one perfluorinated hydrocarbon may be obtained by (a) perfluorinating a material comprising a linear or branched hydrocarbon, a partially fluorinated linear or branched hydrocarbon, or a mixture thereof by electrochemical fluorination (ECF) in an electrochemical cell (ECF cell), to yield an ECF effluent comprising a mixture containing at least one perfluorinated hydrocarbon and (b) separating a material containing at least one perfluorinated hydrocarbon from the ECF effluent.

BRIEF DESCRIPTION OF THE FIGURES

The pyrolysis of fluorinated carbons to produce TFE requires the generation of a reactive fluorinated carbon fragment, difluorocarbene ($:CF_2$). Upon quenching difluorocarbenes may dimerise to produce TFE ($C_2F_4$). To have a high yield of TFE a process is required that leads to the formation of $:CF_2$, the TFE precursor, in good yields and converts them to TFE. Hence, there is the need for a process that generates $:CF_2$ in good yields at comparatively low temperatures to reduce the energy costs.

Surprisingly it has now been found that difluorocarbenes can be formed by the pyrolysis of a perfluorinated materials, in particular perfluorinated hydrocarbons, at low temperatures in the presence of molecular hydrogen. The difluorocarbenes recombine under those conditions to tetrafluorethene. The process provided herein can thus be run at reduced energy costs.

The processes provided herein may, in some embodiments, eliminate the need for using chlorinated raw materials and thus eliminate hydrochloric acid waste streams and chlorinated by-products.

The processes can be run, in other embodiments, as integrated processes comprising a unit generating perfluorinated materials and a unit pyrolysing the perfluorinated materials.

The processes can also be designed, in yet further embodiments, as a so-called closed-loop in which no or very low amounts of waste material is created. The closed-loop processes are therefore environmentally advantageous.

The process of the present description may produce tetrafluoroethene (TFE) and/or hexafluoropropene (HFP) and can thus be used to make both TFE and HFP if desired.

FIG. 1 shows schematically one embodiment where the process is represented as an integrated process of generating a perfluorinated starting material and pyrolysing it to form TFE and/or HFP. The process represented in FIG. 1 is also a closed-loop process. A hydrocarbon feedstock is electrochemically fluorinated in an electrochemical fluorination (ECF) cell (10). Although not shown in FIG. 1, instead of electrochemical fluorination, direct fluorination of the hydrocarbon feed material may be used The lower boiling fluorocarbons are separated (11) from the off-gas, mainly hydrogen, stream 10*a*, and optionally further separated into perfluorinated materials to be fed in the pyrolysis furnace (20), stream 11*a*, and partially fluorinated compounds to be fed back to the ECF cell (10), stream 11*b*.

The higher boiling fluorinated chemical compounds are separated from the ECF effluent or so-called brine of the ECF cell (12), stream 10*b*. These fluorinated compounds are further separated in perfluorinated materials to be fed as the perfluorinated feed material in the pyrolysis furnace (20) and partially fluorinated compounds that are fed back to the ECF cell (10), stream 12*b*.

Hydrogen is fed into the pyrolysis furnace, stream 40. The hydrogen may be from an external source or it may contain or even consist off hydrogen off gas from the ECF effluent. Hydrofluoric acid, HF, which is generated in the pyrolysis can be fed back to the ECF cell (stream (50)).

The perfluorinated compounds of stream 11a and 12a are pyrolyzed in a pyrolysis chamber (20) in the presence of hydrogen. The reaction mixture generated in the pyrolysis zone (20) is subsequently quenched. The quenched gases, stream 20a, are subjected to distillation (30) yielding TFE and/or HFP, and any undesired by-products may be separated and fed back to the pyrolysis furnace (20), stream 30b.

FIG. 1 is not to scale and is intended to be merely illustrative and non-limiting.

DETAILED DESCRIPTION

Before any embodiments of this disclosure are explained in detail, it is to be understood that the disclosure is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. Contrary to the use of "consisting", the use of "including," "containing", "comprising," or "having" and variations thereof is meant to encompass the items listed thereafter. However, in both cases, technical equivalents of the words described by using the limiting term "consisting" or the non-limiting term "including", "containing", "comprising," or "having" and variations thereof are meant to be encompassed. The use of "a" or "an" is meant to encompass "one or more". Any numerical range recited herein is intended to include all values from the lower value to the upper value of that range. For example, a concentration range of from 1% to 50% is intended to be an abbreviation and to expressly disclose the values between the 1% and 50%, such as, for example, 2%, 40%, 10%, 30%, 1.5%, 3.9% and so forth.

As used herein the term "fluorinated compounds" refers to chemical compounds having at least one carbon-bonded hydrogen replaced by fluorine, and specifically includes perfluorinated compounds and partially fluorinated compounds. As used herein the term "perfluorinated hydrocarbon" refers to compounds derived from hydrocarbons but where essentially all carbon-bonded hydrogens have been replaced by fluorines. For example, $CF_4$ is referred to as perfluoromethane and a —$CF_3$ residue is referred to as a perfluormethyl residue. Partially fluorinated hydrocarbons are compounds derived from hydrocarbons where not all hydrogens are replaced by fluorines but at least one of the carbon-bound hydrogen atoms remain. For example, a —$CFH_2$ or a —$CF_2H$ group would both be partially fluorinated methyl groups.

The processes provided herein provide difluorocarbenes by pyrolysis of a perfluorinated material in the presence of hydrogen. The process can be carried out to give good yields of difluorocarbene, for example yields greater than 5% or greater than 20% or even greater than 30% of difluorocarbene based on the amounts of moles perfluorinated hydrocarbons used in the reaction. Such yields may be reached when the pyrolysis is carried out a temperatures as low as about 330° C. (603K) preferably as low as about 350° C. (623K) or at a temperature range of from about 350° C. (623K) to about 1400° C. (1673K) or to about 1,200° C. (1473K) or between 500° C. (773K) and about 1000° C. (1273K) or from about 327° C. (600K) to about 1727° C. (2,000K) or from about 427° C. (700K) to about 1022° C. (1295K). By quenching of the reaction mixture produced in the pyrolysis reaction perfluorinated olefins, in particular those selected from tetrafluoroethene and hexafluoropropene, may be formed.

The process will now be described in greater detail.

Perfluorinated Starting Material

A variety of perfluorinated materials may be subjected to pyrolysis. The material may be a solid, a gas, a liquid, or a mixture thereof. Preferably, the material is a gas or a liquid or a mixture thereof. When the material is a perfluorinated hydrocarbon compound, in some embodiments, it has a boiling point of not more than 250° C.

The perfluorinated starting material generally comprises or consists of at least one linear or branched cyclic or non-cyclic perfluorinated hydrocarbon compound. Typically, the starting material comprises a mixture comprising two or more different perfluorinated hydrocarbons. The material may also comprise partially fluorinated linear or branched hydrocarbon compounds or mixtures thereof. Preferably, the perfluorinated starting material will be substantially free of chlorine, bromine, or iodine containing materials as these create undesirable waste material. "Substantially free" means that the starting material is either free of (contains 0% of a material) or contains a material in amount of not more than 1 or 2% by weight relative to the total weight of starting material. The process provides for the use of mixtures of compounds as the starting material and these mixtures may be complex in that they contain a large variety of different compounds.

The perfluorinated starting material may comprise or consists of a straight chain or branched perfluoroalkane. Examples include but are not limited to an alkane of the formula, $C_nF_{2n+2}$, wherein n is selected from (i) from 1 to 25, or (ii) 1, or (iii) from 2 to 10, or (iv) from 3 to 8; or (v) from 2 to 25. The starting material may also include one or more partially fluorinated analogues thereof (e.g., alkanes according to the formula $C_nH_xF_y$, wherein x is at least 1 and x+y=2n+2). However, the amount of partially fluorinated compounds in the starting material is preferably less than 20% by weight (wt.) or less than 10% by weight. Preferably, the perfluorinated starting material contains at least 50% (wt), or at least 60% (wt) or at least 90% (wt) or at least 95% (wt) of perfluorinated hydrocarbons. In one embodiment the perfluorinated starting material comprises from at least 50% (wt), or at least 60% (wt) or at least 90% (wt) or at least 95% (wt) of perfluorinated hydrocarbons of the formula, $C_nF_{2n+2}$, wherein n is from 2 to 10 or from 3 to 10. Examples of perfluorinated hydrocarbons include but are not limited to tetrafluoromethane, hexafluoroethane, perfluoropropanes, perfluorobutanes, perfluoropentanes, perfluorohexanes, perfluoroheptanes, perfluorooctanes. The perfluorinated starting materials may be obtained, for example by direct fluorination or by electrochemical fluorination or both, optionally followed by purification.

In one embodiment the perfluorinated starting material is the effluent of the electrochemical fluorinated of hydrocarbons, as will be described in greater detail below. The effluent material may be purified to reduce or eliminate the amount of non-fluorinated or partially fluorinated compounds or to remove off-gas. In another embodiment the starting material is obtained by direct fluorination, e.g. the direct fluorination of carbon to give tetrafluoromethane (as described, for example in U.S. Pat. No. 5,611,896).

Pyrolysis

Pyrolysis is the thermal fragmentation of the perfluorinated materials, also referred to as heat cracking. The pyrolysis is carried out in a pyrolysis reactor or furnace ((20), FIG. 1), or more particular in a zone thereof where the temperatures required for the cracking reaction to take place are reached.

The pyrolysis reactors may be chambers, pipes, furnaces and the like. Heating of the pyrolysis zone or reactor can be achieved from external sources, like electric power or superheated steam. A modern technology includes inductive heating via microwaves. The needed powerful microwave generators are commercially available. Frequencies are usually at about 50 to 3000 kHz. Temperatures typically in the range of up to about 3000° C. can be achieved by microwave heating. Inductive heating via microwaves is described, for example, in WO 01/58584. The pyrolysis reaction in microwave reactors may be conducted in the presence of microwave-active materials, i.e. materials capable of absorbing microwave irradiation. Microwave active materials typically heat up upon irradiation by microwaves by absorbing the microwave irradiation. For example, microwave-active particles may heat up by at least 10° C., preferably at least 20° C. and more preferably at least 30° C. when submitting 1 g of the microwave-active material at ambient conditions (25° C., 1 bar) to microwave irradiation of 0.7 kW for 5 minutes. Microwave-active materials include, but are not limited to graphite, carbides, silicides, borides, nitrides, metal oxides, metal hydroxides, metal halides, in particular metal chlorides, metal fluorides. Specific examples include but are not limited to silicon carbides, boron carbides, titanium carbides, zirconium carbides, molybdenum silicides, titanium borides, sodium chloride, magnesium chloride, potassium chloride, cobalt fluorides, potassium fluoride, calcium fluoride and combinations thereof. Other examples include metals or metal alloys such as but not limited to Ni, Pt, Co, Pt/Cu, Pt/Re alloys, chromates, titanates and combinations thereof. These materials may be used in particulate form, for example as particles in a fluidized bed in which case the reaction may be carried out in a fluidized bed reactor. The particles may have an average size (number average) of from about 100 μm to about 5 mm. The fluidized bed may be generated by the reaction components or mixtures or a carrier gas.

Another method for achieving pyrolysis is the Direct Current (DC) Plasma technology as described for example in U.S. Pat. No. 5,611,896. A carrier gas is needed to maintain the flame between the electrodes.

The pyrolysis proceeds in the presence of hydrogen. The molar ratio of hydrogen to perfluorinated hydrocarbons in the pyrolysis zone is from about 0.1 mol to 8 mol hydrogen per 1 mole perfluorinated hydrocarbon, such as, for example from about 0.5 mol to 5 mol hydrogen per 1 mol perfluorinated hydrocarbon(s), or, preferably from about 0.8 to about 2.5 mol hydrogen per 1 mol perfluorinated hydrocarbon(s).

In case mixtures of perfluorinated hydrocarbons are used as perfluorinated material the sum of the molar amount of the perfluorinated hydrocarbons present may be used to determine the ratio of hydrogen to perfluorinated hydrocarbons. An average of the molar amount (geometric means) of the components present may also be used as the molar amount of the perfluorinated hydrocarbons.

The molar ratio present in the pyrolysis zone can be achieved by feeding the hydrogen and the perflourinated materials in the molar ratios or molar flow rates as described above.

The perfluorinated starting material may be fed into the pyrolysis zone continuously or batchwise. One or more carrier gas(es) may be used to feed the starting material into the pyrolysis zone (and out of it). Such carrier gases may be inert gases, such as for example noble gases (e.g. Ar, Kr, Xe, Ne, Rn, He) or nitrogen. Hydrogen may also be used as carrier gas, in which case the perfluorinated material may be fed in a combined stream with the hydrogen into the reactor. The perfluorinated compounds are preferably fed in the pyrolysis reactor and into the pyrolysis zone as gases mostly under sub-atmospheric pressure.

When using hydrogen in the amounts or molar ratios as described above the pyrolysis reaction to generate difluorocarbenes in good yields (e.g., yields of at least 10 mol % or at least 30 mol % based on the molar amount of perfluorinated hydrocarbons) can already take place at temperatures as low as about 300° C. (573K). Therefore, the pyrolysis reaction is preferably carried out at temperatures between about 300° C. (573 K) and about 1400° C. (1673K), preferably between about 320° C. (593K) and about 1300° C. (1573K) and more preferably between about 350° C. (623K) and about 900° C. (1173K) or between about 600° C. (873K) and about 1200° C. (1473K). Under these conditions the perfluorinated materials are heat-cracked. The perfluorinated compounds fragment under these conditions prevailingly into difluoro carbenes (:CFA Difluorocarbenes are reactive species. They may react in the plasma predominantly to $C_2F_4$. By quenching the product stream immediately after it exits the plasma zone defragementation reactions of $C_2F_4$ can be stopped to increase the yield of TFE. Preferably, the reaction is carried out in a way that the reactants are present in the plasma zone only for a short time. This can be achieved by appropriately dimensioning the reactor or the plasma zone or by adapting the flow rate of the reactants. Preferably, the flow rates are from about 0.01 to about 1000 the reactor/volumes per minute (or volumes of the pyrolysis zone per minute) or 0.05 to about 100 reactor volumes per minute (or volumes of the pyrolysis zone per minute).

An advantage of the process using hydrogen is that the pyrolysis can proceed without requiring the addition of carbon. Typically, in processes of the prior art carbon is added, for example as a heat packing material, or injected as powder to adapt for stoichiometric imbalances, which is cumbersome and also increase the process costs. This can be avoided by using a hydrogen stream.

The pyrolysis may be carried out in the presence of catalysts. Suitable catalysts include materials that may generate radicals. Examples include platinum or other metals that may generate radicals in the presence of hydrogen at the temperatures used in the pyrolysis reaction. Such catalysts may be added or may be incorporated in the reactor, for example in the interior of the reactor.

Quenching

The hot reaction mixture obtained by the pyrolysis reaction is subsequently quenched. Typically, it is subjected to rapid cooling. Depending on the temperatures used in the pyrolysis the reaction mixture is quenched to temperatures below 400° C., generally below 300° C. and preferably below 100° C. (in particularly when pyrolysis temperatures of about 300° C. are used. Typically, the mixture is subjected or cooled to these temperatures within less than a second, preferably in less than 0.1 seconds after exiting the pyrolysis zone. Cooling rates of $10^4$-$10^5$ K/sec may be used. These high cooling rates can be achieved either by conducting the hot reaction mixture through a bundle of pipes which are externally cooled or by injecting a coolant in the reaction mixture. The latter technology is also called wet quenching, the former dry quenching. Cold gases or liquids, like liquid perfluorinated carbons or water can be used as coolant. Quenching leads to the formation of TFE. The efficiency of the quench process generally controls the selectivity of TFE. The higher the cooling rate the higher the selectivity and the less coking. Coking is formation of carbon arising via disproportionation of $:CF_2$ into carbon and $CF_4$. Coking interferes with the quench process. Suitable quenching processes are described, for example, in WO 2004/061160 A1.

Separation

TFE and/or HFP can be isolated from the quenched mixture of gases (stream 20*a*) for example by distillation (30). The quenched mixture mainly contains TFE and/or HFP but may also contain perfluoroisobutylene (PFIB) and saturated perfluoroalkanes like $CF_4$, $C_2F_6$, or octafluorocyclobutane. In contrast to the commonly used "chlorine" process via R-22, hydrogen and chlorine containing chemical compounds are virtually absent. This renders the separation of TFE and HFP via distillation relatively simple in comparison to the R-22 process even when TFE is to be used in a subsequent polymerization to produce PTFE, where a high purity is desired. Due to the absence of chlorinated materials only few distillation columns may be needed to purify TFE and HFP from by-products, such as "low boiling" components like $CF_4$, $C_2F_6$, cyc. $C_4F_8$ and higher boiling components like PFIB (perfluoroisobutylene). The distillation cuts of these side products can be fed back to the pyrolysis e.g., stream 30*b*, FIG. 1.

Electrochemical Fluorination

In a particular embodiment the perfluorinated starting material, such as the perfluorinated hydrocarbons, used in the processes described herein is obtained by the electrochemical fluorination (ECF) of a hydrocarbon feedstock, for example in an electrochemical cell (ECF cell), optionally after some purification.

Generally any electrochemical fluorination process can be used to perfluorinate the starting material. Various processes that may be used are described or referenced in WO 2004/061160 A1, such as for example, the Simons electrochemical fluorination process, the interrupted current process, the bipolar flow cell, the SOLUTIA EHD process, and the like.

The Simons electrochemical fluorination (Simons ECF) process comprises passing a direct electric current through an electrolyte, (i.e., a mixture of fluorinatable organic starting compound, liquid anhydrous hydrogen fluoride, and perhaps a conductivity additive), to produce the desired fluorinated compound or fluorochemical. Simons ECF cells typically utilize a monopolar electrode assembly, i.e., electrodes connected in parallel through electrode posts to a source of direct current at a low voltage (e.g., four to eight volts). Simons ECF cells are generally undivided, single-compartment cells, i.e., the cells typically do not contain anode or cathode compartments separated by a membrane or diaphragm.

Simons ECF can be carried out essentially as follows. A starting material and an optional conductivity additive are dispersed or dissolved in anhydrous hydrogen fluoride to form an electrolytic "reaction solution." One or more anodes and one or more cathodes are placed in the reaction solution and an electric potential (voltage) is established between the anode(s) and cathode(s), causing electric current to flow between the cathode and anode, through the reaction solution, and resulting in an oxidation reaction (primarily fluorination, i.e., replacement of one or more carbon-bonded hydrogens with carbon-bonded fluorines) at the anode, and a reduction reaction (primarily hydrogen evolution) at the cathode. As used herein, "electric current" refers to electric current in the conventional meaning of the phrase, the flow of electrons, and also refers to the flow of positively or negatively charged chemical species (ions).

Generally the Simons ECF process is practiced with a constant current passed through the electrolyte; i.e., a constant voltage and constant current flow. The current passing through the electrolyte causes one or more of the hydrogens of the starting material to be replaced by fluorine.

A useful electrochemical fluorination cell includes the type generally known in the electrochemical fluorination art as a flow cell. Flow cells comprise a set (one of each), stack, or series of anodes and cathodes, where reaction solution is caused to flow over the surfaces of the anodes and cathodes using forced circulation. These types of flow cells are generally referred to as monopolar flow cells (having a single anode and a single cathode, optionally in the form of more than a single plate, as with a conventional electrochemical fluorination cell), and, bipolar flow cells (having a series of anodes and cathodes). U.S. Pat. No. 5,322,597 (Childs et al.) describes the practice in a bipolar flow cell of an electrochemical fluorination process comprising passing by forced convection a liquid mixture comprising anhydrous hydrogen fluoride and fluorinatable organic compound at a temperature and a pressure where a substantially continuous liquid phase is maintained between the electrodes of a bipolar electrode stack. The bipolar electrode stack comprises a plurality of substantially parallel, spaced-apart electrodes made of an electrically conductive material, e.g., nickel, which is essentially inert to anhydrous hydrogen fluoride and when used as an anode, is active for electrochemical fluorination. The electrodes of the stack are arranged in either a series or a series-parallel electrical configuration. The bipolar electrode stack has an applied voltage difference that produces a direct current that can cause the production of fluorinated organic compound.

Another example of a bipolar flow cell is the Solutia EHD (electrohydrodimerisation) cell. In the interrupted current electrochemical fluorination process generally a reaction solution is prepared that comprises hydrogen fluoride and a starting material. The hydrogen fluoride is preferably anhydrous hydrogen fluoride, meaning that it contains at most only a minor amount of water, e.g., less than about 1 weight percent (wt %) water, preferably less than about 0.1 weight percent water. The reaction solution within the ECF cell includes an electrolyte phase comprising HF and an amount of starting material dissolved therein. In general, the starting material is preferably to some degree soluble or dispersible in liquid hydrogen fluoride. Gaseous starting materials can be bubbled through the hydrogen fluoride to prepare the reaction solution, or charged to the cell under pressure. Solid or liquid starting materials can be dissolved or dispersed in the hydrogen fluoride. Starting materials that are relatively less soluble in hydrogen fluoride can be introduced to the cell as a solute dissolved in a fluorochemical fluid.

The reaction solution is exposed to reaction conditions (e.g., temperature, pressure, electric voltage, electric current, and power) sufficient to cause fluorination of the starting material. Reaction conditions chosen for a particular fluorination process depend on factors such as the size and construction of the ECF cell, the composition of the reaction solution, the presence or absence of a conductivity additive, flow rate, etc. The reaction temperature can be any temperature that allows a useful degree of fluorination of the starting material. The temperature may depend on the factors discussed in the preceding paragraph, as well as the solubility of the starting material and the physical state of the starting material or the fluorinated product. The electricity passed through the reaction solution can be any amount that will result in fluorination of the starting material. The current is preferably insufficient to cause excessive fragmentation of the starting material or to cause the liberation of fluorine gas during fluorination.

The ECF effluent can be separated using conventional techniques such as, for example, distillation. Typically, the off gas generated by the ECF, which generally is hydrogen, is separated, for example by a membrane process. The fluorinated components of the ECF effluent may be further purified or used as obtained. The perfluorinated material is then fed to the pyrolysis. The insufficiently fluorinated compounds may be returned to the ECF cell for perfluorination.

Membrane Process/Separation

The ECF cell may have one or more membrane systems to capture the off-gas. Typically the off-gas is molecular hydrogen ($H_2$). Some fluorine-containing compounds (i.e., perfluorinated and non-perfluorinated compounds) are typically carried over by the off-gas. A membrane process can be used to capture the partially fluorinated and perfluorinated compounds and then the partially fluorinated compounds can be fed back into the ECF cell. By introducing membrane separation, only $H_2$ is released from the overall process, advantageously resulting in a closed-loop process. The hydrogen gas released may find further use in generating energy for the process or to provide energy elsewhere in a manufacturing plant, or may be used in the pyrolysis of the perfluorinated material.

Membranes separate gases by the principle of selective permeation across the membrane wall. For polymeric membranes, the rate of permeation of each gas is determined by its solubility in the membrane material and the rate of diffusion through the molecular free volume in the membrane wall. Gases that exhibit high solubility in the membrane and gases that are small in molecular size, permeate faster than larger, less soluble gases.

The output from the ECF process includes a large volume of hydrogen, perfluorinated product, and partially fluorinated materials. The membrane process separates the hydrogen from the fluorinated species by allowing the smaller, more soluble hydrogen to pass through the membrane while concentrating the fluorinated material (permeate). Suitable membranes are commercially available. One commercially available membrane is the MEDAL™ Gas-separation membrane available from Air Liquide, Houston, Tex., USA. Alternatively, a cryogenic distillation process may be used to separate the off-gas ($H_2$). The fluorinated materials may be used as perfluorinated starting material in the pyrolysis reaction or it may be further purified, for example by distillation to enrich the perfluorinated hydrocarbon content and/or to remove partially fluorinated materials. The partially fluorinated materials can be fed back into the ECF unit.

Starting Materials for the EFC

A variety of materials can be used as the starting materials for ECF. The starting material can be a gas, a liquid, or a mixture thereof. The starting material generally comprises linear or branched hydrocarbon compounds, partially fluorinated linear or branched hydrocarbon compounds or mixtures thereof. The linear or branched hydrocarbon compound generally consists of carbon and hydrogen but hydrocarbon compounds having one or more substituents such as hydroxy, amino groups, carboxy groups, sulphonic acid groups and amide groups may be used. Preferably, however the starting material will be substantially free of chlorine, bromine, or iodine containing materials as these create undesirable waste material. "Substantially free" means that the starting material is either free of (contains 0%) or contains a material in amount of not more than 1 or 2% by weight relative to the total weight of starting material. The starting material may contain cyclic compounds, such as cyclic hydrocarbons in admixture with the linear or branched (partially fluorinated) hydrocarbon compounds. Mixtures of compounds may also be used as the starting material. The starting material is chosen such that the desired perfluorinated materials for the pyrolysis reaction will be formed in satisfying amounts. Preferably, the starting material comprises a straight or branched alkane that is entirely hydrocarbon (e.g., a straight chain alkane, $C_nH_{2n+2}$, wherein n is from about 1 to 25, preferably from about 4 to about 8 or about 10, and more preferably n is 4 to 6), or, a partially fluorinated analog thereof (e.g., $C_nH_xX_y$, wherein X is fluorine, and wherein x is at least 1 and x+y=2n+2). The hydrocarbon compound may comprise saturated and unsaturated compounds including olefins and aromatic compounds such as benzene, toluene, or xylene. Examples of especially preferred starting materials include methane, ethane, propane. butane, pentane, hexane, heptane, and octane and hydrocarbons up to 10 carbons and mixtures thereof, and mixtures of hydrocarbons with olefins (e.g., isobutylene, etc.). A particular hydrocarbon starting material includes crude oil and petroleum fractions, so-called distillation cuts originating from refining of crude oil and from making olefins such as ethylene and propylene. Preferably, the boiling point of these petroleum fractions is not more than 200° C., and more preferably not more than 150° C. or 100° C. To keep the overall ECF cell pressure low, preferably the gaseous starting material has a boiling point of at least −50° C. and is easy to liquefy, e.g., propane (b. p. −42° C.), propene (b. p. −47° C.), butane (b. p. 0° C.), butene (b. p. −6° C.), isobutylene (b. p. −7° C.). To ensure a fast and complete fluorination, the liquid starting materials are preferably compounds having 10 carbon atoms or less; otherwise the fluorination proceeds slowly and extensive branching and fragmentation can occur, which makes the separation step more difficult. Mixtures of hydrocarbons and their isomers and olefins may be added to the ECF cell as starting materials.

In an alternative method the perfluorinated material may be obtained by the direct fluorination of carbon of hydrocarbons as described, for example, in U.S. Pat. No. 5,611,896.

The process of the present invention is preferably designed as a closed-loop process where all perfluorinated compounds can be converted into fluoroolefins and all undesired byproducts (e.g., C—H containing/partially fluorinated materials) can be recycled until completion. This reduces the process cost and fluorinated compounds in waste streams. Thus, the process of the present invention is environmentally responsible.

The process can be designed as an integrated process comprising a unit generating perfluorinated materials, such as, for example, an ECF cell, and a unit pyrolysing the perfluorinated materials. This integrated process may also be designed as a closed-loop process.

Therefore, in one embodiment there is provided a process comprising a unit generating perfluorinated materials and a pyrolysis unit generating difluorocarbenes and perfluorinated olefins such as tetraflurorethene. Both units may contain separation or purification units. Therefore in one embodiment there is provided a process for manufacturing TFE/HFP comprising the steps of (1) perfluorinating a linear, branched, cyclic hydrocarbon or hydrocarbon mixtures by direct fluorination or by electrochemical fluorination (ECF) to yield an effluent stream containing a perfluorinated material, optionally, at least partially separating the perfluorinated material from the effluent, and (2) pyrolyzing said perfluorinated material in the presence of hydrogen at a molar ratio of hydrogen to perfluorinated material of is from about 0.7:1.0 to about 0.7:8.0 and at temperatures greater than about 300° C. and up to about 1,300° C. to yield a reaction mixture containing difluorocarbene, (3) quenching said reaction mixture to form a product mixture containing fluorinated olefins, (4) recovering TFE/HFP from said product mixture and optionally separating HF from the product mixture and feeding it back to the ECF cell, wherein the reaction conditions, starting materials, purifications steps and equipment can be used as described above.

Figure 1:
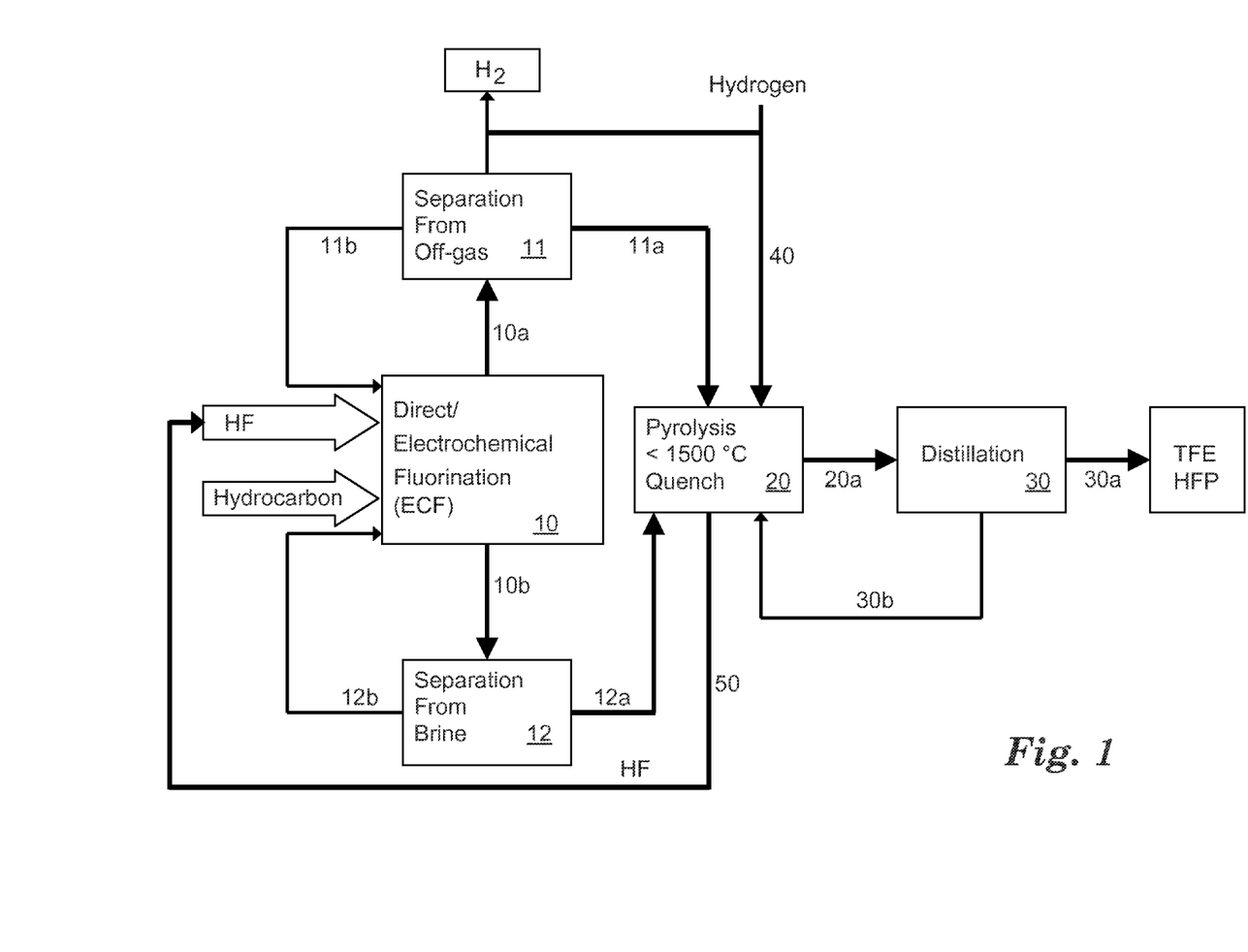

For example, an integrated process of generating and pyrolising perfluorinated hydrocarbons can be carried out as follows, using perfluorooctane as an example for a perfluorinated hydrocarbon. Such a process is exemplified in FIG. 1. In a first step the perfluorinated material is generated. This can be achieved, for example, by the electrochemical fluorination of octane, which can be carried out as described in WO2004/061160 example 1. This part is shown in FIG. 1 where HF and a hydrocarbon feedstock (here octane) are fed in the ECF cell 10. The off-gas stream 10a may then be fed to a membrane process (11). The membrane process as described in WO2004/061160 may be used. The off-gas may be used for other purposes or may be used in the subsequent pyrolysis reaction (stream 40). Fluorinated material separated from the off gas may be fed into directly into the pyrolysis chamber (stream 11a) or it may be further purified prior to being subjected to the pyrolysis reaction. The ECF effluent 10b can be fed to the separation process 12, which may comprise distillation to separate perfluorinated materials (perfluorooctane) from partially fluorinated materials. Partially fluorinated by-products may be collected and fed back (stream 12b) into the electrochemical fluorination unit (10). The perfluorinated material may then be fed (stream 12a) into a pyrolysis chamber (20). However, it may also be possible not to purify the effluent but to use it as is in the pyrolysis because the hydrogen off-gas may be used for this purpose. In such embodiment further hydrogen may be added or perfluorinated materials may be added or off-gas hydrogen may be removed to generate the desired molar ratio for the pyrolysis reaction. The perfluorinated material is pyrolysed in the presence of hydrogen (stream 40) in the pyrolysis zone of the pyrolysis chamber (20). The feed rates are adjusted such that hydrogen is present in the pyrolysis chamber in the desired molar ratios with respect to the perfluorinated material. A 30 kW DC plasma torch as described in WO 01/58841 can be used to generate a plasma in the pyrolysis chamber. No carbon needs to be added. Alternatively, a microwave reactor may be used. The temperature in the pyrolysis zone is adjusted to the desired range. The resulting reaction mixture is dry-quenched immediately after exiting the pyrolysis zone. Dry quenching can be carried out as described on WO2004/061160. The product mixture obtained by quenching is then fed (stream 20a) into the separation process 30, which typically is a simple distillation or a sequence of distillations. The desired products TFE and/or HFP are separated out (30a). The undesirable fluorine-containing products 30b are returned to the pyrolysis furnace for further processing. HF generated by the pryolysis can also be fed back into the ECF unit (10).

The following list of exemplary embodiments illustrates various specific features, advantages, and other details of the invention. The particular materials and amounts recited in these exemplary embodiments, as well as other conditions and details, should not be construed in a manner that would unduly limit the scope of this invention.

1. A process comprising pyrolyzing at least one perfluorinated hydrocarbon, or a material containing at least one perfluorinated hydrocarbon, in a pyrolysis zone at a temperature between about 600 K and about 2000 K in the presence of hydrogen to yield a reaction mixture containing difluorocarbene, wherein the hydrogen is present in the pyrolysis zone in a molar ratio of hydrogen to perfluorinated hydrocarbons of from about 0.1 to 8 mol hydrogen to 1 mol of perfluorinated hydrocarbon(s).

2. The process of embodiment 1 wherein the pyrolysis is carried at in the pyrolysis zone at a temperature of from about 600 K to about 1250 K.

3. The process of embodiments 1 or 2 further comprising quenching said reaction mixture to yield a product mixture containing tetrafluoroethene and/or hexafluoropropene.

4. The process of embodiment 3, further comprising separating tetrafluoroethene and/or hexafluoropropene from said product mixture.

5. The process according to any one of the preceding embodiments wherein said at least one perfluorinated hydrocarbon is a gas, a liquid, or a mixture thereof.

6. The process according to any one of the preceding embodiments wherein said at least one perfluorinated hydrocarbon comprises a straight or branched perfluroalkane represented by the formula $C_nF_{2n+2}$, wherein n is an integer of from 1 to 25, or 1, or from 2 to 10, or from 2 to 20, or from 3 to 8.

7. The process according to embodiment 6, wherein n is an integer of from about 4 to about 10.

8. The process according to any one of the preceding embodiments, wherein the at least one perfluorinated hydrocarbon has a boiling point of not more than 250° C.

9. The process according to any one of the preceding embodiments wherein the at least one perfluorinated hydrocarbon is linear.

10. The process according to any one of the preceding embodiments wherein the pyrolysis is carried out in the absence of added carbon.

11. The process according to any one of the preceding embodiments wherein at least a part of the product mixture after removing tetrafluorethene and/or hexafluoropropene is fed back into the pyrolysis zone.

12. The process according to any one of the preceding embodiments wherein difluorcarbene is generated at a yield of at least 30%.

13. The process according to any one of the preceding embodiments wherein the material containing at least one perfluorinated hydrocarbon is obtained by
   (a) perfluorinating a material comprising a linear or branched hydrocarbon, a partially fluorinated linear or branched hydrocarbon, or a mixture thereof by electrochemical fluorination (ECF) in an electrochemical cell (ECF cell), to yield a mixture containing at least one perfluorinated hydrocarbon and
   (b) separating a material containing at least one perfluorinated hydrocarbon from said ECF effluent.

14. The process according to embodiment 13 wherein said linear or branched hydrocarbon corresponds to the formula $C_nH_{2n+2}$ or mixture thereof wherein n is an integer of from 2 to 25 or from 2 to 10 or from 3 to 20 or from 3 to 8.

15. The process according to embodiment 13 wherein said linear or branched hydrocarbon corresponds to the formula $C_nH_{2n+2}$ or mixture thereof and n represents an integer from 4 to 10.

16. The process according to any one of embodiments 13 to 15 wherein said ECF effluent is separated by distillation.

17. The process according to any one of embodiments 13 to 16, wherein said ECF effluent comprises an off-gas containing or consisting of hydrogen, and further comprising feeding that off-gas into the pyrolysis zone.

18. The process according to any one of embodiments 13 to 17 wherein said ECF effluent comprises a partially fluorinated material and wherein said partially fluorinated material is separated from said off-gas and re-introduced in said ECF cell as starting material.

19. The process according to any one of the preceding embodiments wherein the pyrolysis zone is part of a microwave reactor.

20. The process according to any one of the preceding embodiments wherein the pyrolysis zone is part of a fluidized bed reactor.

21. The process according to any one of the preceding embodiments wherein the pyrolysis zone is part of a microwave fluidized bed reactor and contains microwave active particles.

22. The process according to any one of the preceding embodiments wherein the pyrolysis zone contains one or more catalysts catalysing the generation of radicals.

23. The process according to any one of the preceding embodiments wherein the presence of hydrogen to perfluorinated hydrocarbon(s) is achieved by feeding hydrogen and perfluorinated hydrocarbons into the pyrolysis zones in the molar ratios as defined in embodiment 1.

The following examples illustrate various specific features, advantages, and other details of the invention. The particular materials and amounts recited in these examples, as well as other conditions and details, should not be construed in a manner that would unduly limit the scope of this invention. All parts, percentages, and ratios are by weight unless otherwise specified.

EXAMPLES

Pyrolysis experiments were conducted in shock wave tubes having an inner diameter of 10 cm as model system for a pyrolysis reactor. The shock tubes were heated by an electrical mantle and contained an observation window for continuous recording by a UV spectrometer. The shock tube experiments were carried out as described in K. Glanzer and J. Troe, Helvetica Chimica Acta 1972, 55, 2884. In shock tube experiments test a reactant mixture of perfluorinated hydrocarbon, hydrogen and an inert carrier gas or diluent (argon) was fed into the low pressure section of the shock tube. The high pressure section contained hydrogen as the driver gas. The driver gas does not come into contact with the reactant mixture in the low pressure section within the observed part of the test mixture. Low and high pressure sections are separated by an aluminium diaphragm. By increasing the pressure of the driver gas the diaphragm breaks and a shock wave is generated which propagates into the low pressure section of the tube (front shock wave). The shock wave heats and compresses the reactant mixture in the incident wave. The incident wave is reflected at the end of the tube and forms a reflected wave by which the reactant mixture is heated and compressed a second time. The temperatures and pressure reached in the reactant mixture through incident and reflected wave can be calculated from the conditions before the arrival of the shock wave and the supersonic speed of the generated shock wave.

The generation of difluorocarbene was monitored by UV spectroscopy using the absorption signal of ($:CF_2$) at 248 nm, using a high pressure Xe lamp as light source and recording the absorption signal after single passage of the light beam through the shock tube. For the concentration determination the decadic absorption coefficient $\epsilon$ of $:CF_2$ at 248 nm of $1.5\times10^6$ cm$^2$ mol$^{-1}$ was used. Concentration measurements were continuously recorded for 1.5 ms after the arrival of the shockwave at the observation window for which period pressure and temperature of the gas mixture remained essentially constant.

The formation and degradation of $:CF_2$ was continuously recorded for the observation period. The degradation was compared to know reaction constants for possible degradation reactions of difluorocarbenes in the given reaction mixture to model the degradation reaction.

Example 1

Figure 2:
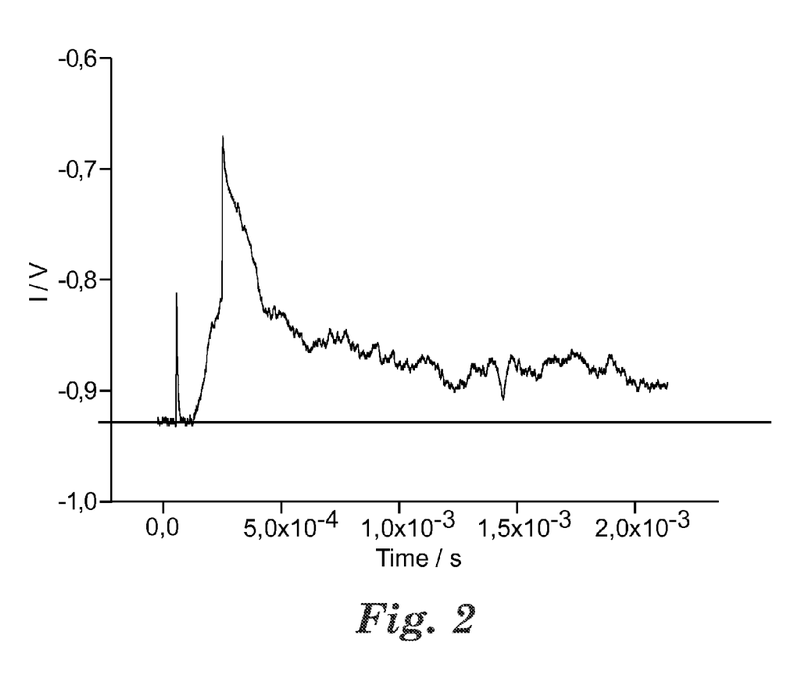
FIG. 2 shows the time profile of difluorocarbene formation and subsequent reaction to form perfluorinated olefins, as described in Example 1.

A mixture of perfluoroethane (1.5 mol percent), hydrogen (1.7 mol percent) and argon (96.8 mol percent) was fed into the high pressure section of the shock tube (total gas concentration was $5.6\times10^{-5}$ mol cm$^{-3}$). The mixture was heated in the incident shock wave (first peak in FIG. 2) to a temperature of 610 K by which after an induction period $:CF_2$ had been formed before the reflected shock wave reached the observation window. The arrival of the reflected wave is indicated by the second peak distinct peak in FIG. 2. The temperature behind the reflected wave was 1010 K. The total gas concentration behind the reflected wave was $1.06\times10^{-4}$ mol cm$^{-3}$. The degradation profile of $:CF_2$ fits well with the velocity constant of the reaction $2:CF_2 \rightarrow C_2F_4$ at 1000K, which is $k=1.3\times10^{17}$ cm$^6$ mol$^{-2}$ s$^{-1}$.

Therefore, example 1 shows that difluorocarbene is formed under these reaction conditions and converted almost quantitatively into TFE.

Example 2

Comparative Example

Example 1 was repeated except that no hydrogen was used. A signal for the formation of $:CF_2$ could not be recorded.

The invention claimed is:

1. A process comprising pyrolyzing at least one perfluorinated hydrocarbon, or a material containing at least one perfluorinated hydrocarbon, in a pyrolysis zone at a temperature between about 580 K and about 2000 K in the presence of hydrogen to yield a reaction mixture containing difluorocarbene, wherein the hydrogen is present in the pyrolysis zone in a molar ratio from about 0.1 to 8 mol hydrogen per mol of perfluorinated hydrocarbon.

2. The process of claim 1 wherein the pyrolysis is carried at in the pyrolysis zone at a temperature of from about from 600 K to 1100 K.

3. The process of claim 1 further comprising quenching said reaction mixture after it exits the pyrolysis zone to yield a product mixture containing tetrafluoroethene and/or hexafluoropropene and, optionally, separating tetrafluoroethene and/or hexafluoropropene from said product mixture.

4. The process according claim 1 wherein the perfluorinated hydrocarbon is a gas, a liquid, or a mixture thereof.

5. The process according to claim 1 wherein the perfluorinated hydrocarbon comprises a straight chain or branched perfluroalkane represented by the formula $C_nF_{2n+2}$, wherein n is an integer of from 2 to 25.

6. The process according to claim 1, wherein the perfluorinated hydrocarbon has a boiling point of not more than 250° C.

7. The process according to claim 1 wherein the pyrolysis is carried out in the absence of added carbon.

8. The process according to claim 1 further comprising quenching the reaction mixture comprising difluorocarbene to yield a product mixture containing tetrafluoroethene and/or hexafluoropropene and feeding back into the pyrolysis zone at least a part of the product mixture after removing tetrafluorethene and/or hexafluoropropene therefrom.

9. The process according claim 1 wherein difluorcarbene is generated at a yield of at least 30 mol % based on the molar amount of perfluorinated hydrocarbons.

10. The process according to claim 1 wherein the material containing at least one perfluorinated hydrocarbon is obtained by
   (a) perfluorinating a material comprising a linear or branched hydrocarbon, a partially fluorinated linear or branched hydrocarbon, or a mixture thereof by electrochemical fluorination (ECF) in an electrochemical cell (ECF cell), to yield an ECF effluent comprising a mixture containing at least one perfluorinated hydrocarbon and
   (b) separating a material containing at least one perfluorinated hydrocarbon from the ECF effluent.

11. The process according to claim 10 wherein the linear or branched hydrocarbon corresponds to the formula $C_nH_{2n+2}$ or mixture thereof and n represents an integer of from 2 to 25.

12. The process according to claim 10 wherein the ECF effluent is separated by distillation.

13. The process according to claim 10, wherein said ECF effluent comprises an off-gas containing hydrogen, and further comprising feeding that off-gas into the pyrolysis zone.

14. The process according to claim 13 wherein the ECF effluent comprises a partially fluorinated material and wherein the partially fluorinated material is separated from the off-gas and re-introduced in said ECF cell as starting material.

15. The process of claim 1, wherein the pyrolysis zone is part of a microwave reactor, a fluidized bed reactor, a microwave fluidized bed reactor or microwave fluidized bed reactor containing microwave-active particles.

* * * * *

UNITED STATES PATENT AND TRADEMARK OFFICE
CERTIFICATE OF CORRECTION

Page 1 of 2

PATENT NO. : 9,139,496 B2
APPLICATION NO. : 13/805561
DATED : September 22, 2015
INVENTOR(S) : Klaus Hintzer It is certified that error appears in the above-identified patent and that said Letters Patent is hereby corrected as shown below:

On The Title Page

Column 1
Line 1 (Assignee), Delete "INNOVATION" and insert -- INNOVATIVE --, therefor.

In The Specification

Column 2
Line 2, Delete "tetrafluorethene" and insert -- tetrafluoroethene --, therefor.
Line 30, Delete "tetrafluorethene." and insert -- tetrafluoroethene. --, therefor.
Line 55, Delete "used" and insert -- used. --, therefor.

Column 3
Line 3, Delete "consist off" and insert -- consist of --, therefor.

Column 5
Line 62, Delete "perflourinated" and insert -- perfluorinated --, therefor.

Column 6
Line 23, Delete "(:CFA" and insert -- (:CF$_2$). --, therefor.
Line 25-26, Delete "defragementation" and insert -- defragmentation --, therefor.

Column 11
Line 2, Delete "diflurocarbene," and insert -- difluorocarbene, --, therefor.
Line 10, Delete "pyrolising" and insert -- pyrolyzing --, therefor.
Line 56, Delete "pryolysis" and insert -- pyrolysis --, therefor.

Signed and Sealed this
First Day of March, 2016

Michelle K. Lee
*Director of the United States Patent and Trademark Office*

Column 12
Line 20, Delete "perfluroalkane" and insert -- perfluoroalkane --, therefor.
Line 36, Delete "tetrafluorethene" and insert -- tetrafluoroethene --, therefor.
Line 39, Delete "difluorcarbene" and insert -- difluorocarbene --, therefor.

In The Claims

Column 14
Line 53, In Claim 4, delete "according claim" and insert -- according to claim --, therefor.
Line 57, In Claim 5, delete "perfluroalkane" and insert -- perfluoroalkane --, therefor.

Column 15
Line 1-2, In Claim 8, delete "tetrafluorethene" and insert -- tetrafluoroethene --, therefor.
Line 3, In Claim 9, delete "according claim" and insert -- according to claim --, therefor.
Line 3, In Claim 9, delete "difluorcarbene" and insert -- difluorocarbene --, therefor.
*